(12) United States Patent
Budzelaar et al.

(10) Patent No.: US 10,549,316 B2
(45) Date of Patent: Feb. 4, 2020

(54) TWO-TERMINAL CMUT DEVICE

(71) Applicant: KONINKLIJKE PHILIPS N.V., Eindhoven (NL)

(72) Inventors: Franciscus Paulus Maria Budzelaar, Eindhoven (NL); Alfons Wouter Groenland, Eindhoven (NL); Antonia Cornelia Van Rens, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 382 days.

(21) Appl. No.: 15/533,715

(22) PCT Filed: Nov. 30, 2015

(86) PCT No.: PCT/EP2015/077995
§ 371 (c)(1),
(2) Date: Jun. 7, 2017

(87) PCT Pub. No.: WO2016/091624
PCT Pub. Date: Jun. 16, 2016

(65) Prior Publication Data
US 2017/0320091 A1 Nov. 9, 2017

(30) Foreign Application Priority Data
Dec. 11, 2014 (EP) .................................. 14197268

(51) Int. Cl.
*B06B 1/02* (2006.01)
*H01L 41/04* (2006.01)
(Continued)

(52) U.S. Cl.
CPC .............. *B06B 1/0292* (2013.01); *A61B 8/06* (2013.01); *A61B 8/4483* (2013.01); *A61B 8/488* (2013.01);
(Continued)

(58) Field of Classification Search
CPC ......... B06B 1/02; B06B 1/0292; H04R 19/00; H04R 19/005; H04R 19/01; H01L 41/00;
(Continued)

(56) References Cited

U.S. PATENT DOCUMENTS 5,423,220 A  6/1995  Finsterwald et al.
5,997,479 A  12/1999  Savord et al.
(Continued)

OTHER PUBLICATIONS

Groenland "Nanolink-Based Thermal Devices: Integration of ALD Tin Thin Films" PHPD Thesis, University of Twente, 2011.
(Continued)

*Primary Examiner* — Edgardo San Martin

(57) ABSTRACT

The invention related to an ultrasound system comprising: an ultrasound array including at least one capacitive micromachined ultrasonic transducer device comprising a membrane coupled to a first electrode, a substrate opposing the membrane with a gas or vacuum cavity there between and coupled to a second and a third electrodes, wherein the second electrode opposes the first electrode in a peripheral region and the third electrode opposes the first electrode in a central region; at least one drive circuit coupled to the array. The system further comprises a high impedance resistor, which electrically couples to the second electrode and the third electrode and has an impedance value higher than an AC impedance between the first and the second electrodes, when the membrane of the CMUT device is in the collapsed state and the CMUT devices is activated at operating frequency.

15 Claims, 5 Drawing Sheets

(51) Int. Cl.
  *A61B 8/00* (2006.01)
  *A61B 8/06* (2006.01)
  *A61B 8/08* (2006.01)
(52) U.S. Cl.
  CPC ....... *B06B 2201/20* (2013.01); *B06B 2201/76* (2013.01)
(58) Field of Classification Search
  CPC ... H01L 41/04; H01L 41/047; H01L 41/0471; H01L 41/0472; H01L 41/0474; A61B 8/12; A61B 8/14; A61B 8/4444; A61B 8/4494; G01L 9/0005; G01L 9/0042; G01L 9/0073
  See application file for complete search history.

(56) References Cited

U.S. PATENT DOCUMENTS

| | | | |
|---|---|---|---|
| 6,013,032 | A | 1/2000 | Savord |
| 6,283,919 | B1 | 9/2001 | Roundhill et al. |
| 6,328,696 | B1 | 12/2001 | Fraser |
| 6,443,896 | B1 | 9/2002 | Detmer |
| 6,458,083 | B1 | 10/2002 | Jago et al. |
| 6,530,885 | B1 | 3/2003 | Entrekin et al. |
| 6,623,432 | B2 | 9/2003 | Powers et al. |
| 8,203,912 | B2 | 6/2012 | Roest et al. |
| 9,383,282 | B2 * | 7/2016 | Besling ................. G01L 9/0042 |
| 10,265,728 | B2 * | 4/2019 | Van Rens ............. B06B 1/0292 |
| 2005/0200241 | A1 | 9/2005 | Degertekin |
| 2008/0173094 | A1 | 7/2008 | Shikata |
| 2010/0198070 | A1 | 8/2010 | Asafusa et al. |
| 2010/0202254 | A1 | 8/2010 | Roest |
| 2010/0249605 | A1 | 9/2010 | Degertekin |
| 2010/0268089 | A1 | 10/2010 | Degertkin |
| 2018/0015504 | A1 * | 1/2018 | Zhao ........................ B06B 1/02 |
| 2018/0071775 | A1 * | 3/2018 | Zhuang ................. B06B 1/0292 |

OTHER PUBLICATIONS

Van Bui et al "Ultra-Thin Atomic Layer Deposited Tin Films: Non-Linear I-V Behaviors and the Imporatance of Surface Passivation" Journal of Nanoscience and Nanotechnology, vol. 11, p. 8120-8215 2011.
Van Bui "Conduction and Electric Field Effect in Ultra-Thin Tin Films" Appl. Phys. Lett. 103, (2013).
Groenland et al "Four Point Probe Structures With Buried and Surface Electrodes for the Electrical Characterization of Ultrathin Conducting Films" IEEE Transactions on Semiconductor Manufacturing, vol. 25, No. 2, 2012.
Guldiken et al "CMUTs With Dual Electrode Structures for Improved Transmit and Receive Performance" IEEE Transactions on Ultrasonics, Ferroelectrics and Frequency Control, IEEE, US vol. 53, No. 2, Feb. 1, 2006, p. 483-491.
J. Schmitz, Microchip post-processing: there is plenty of room at the top, in: Future trends in microelectronics: frontiers and innovations, Eds. S. Luryi, J. M. Xu and A. Zaslaysky, John Wiley & Sons, Hoboken 2013. ISBN 978-1118-44216-6.
Clyde H. Lane, Nichrome Resistor Properties' and Reliability, Rome Air Development Centre, Griffiss Air Force Base, New York 131441 RADC-TR-73-.181, 1973.
Vishay Thin Film technical note, Major Advancements in the Protection of Thin Film Nichrome-Based Resistors with Specialized Passivation Methods (SPM), Document No. 60019, Revision: Feb. 25, 2008, available from www.vishay.com.
Hongchuan Jiang et al, Influences of Film Thickness on the Electrical Properties of TaNx Thin Films Deposited by Reactive DC Magnetron Sputtering, J. Mater. Sci. Technol., 2010, 26(7), 597-600.
H. Van Bui et al, Growth Kinetics and Oxidation Mechanism of ALD TiN Thin Films Monitored by In Situ Spectroscopic Ellipsometry, Journal of The Electrochemical Society, 158 (3) H214-H220 (2011).
H. Van Bui et al, Ultra-Thin Atomic Layer Deposited TiN Films: Non-Linear I-V Behaviour and the Importance of Surface Passivation, Journal of Nanoscience and Nanotechnology, vol. 11, 8120-8125, 2011.
J.H. Klootwijk, MIM in 3D: Dream or reality? (invited), Microelectronic Engineering 88 (2011) 1507-1513.
E. Langereis et al, In situ spectroscopic ellipsometry study on the growth of ultrathin TiN films by plasma-assisted atomic layer deposition, Journal of Applied Physics 100, 023534 (2006).
J. Rölke, Nichrome Thin Film Technology and Its Application, Electrocomponent Science and Technology, 1981, vol. 9, pp. 51-57.
J. Tao et al, Electromigration Characteristics of TiN Barrier Layer Material, IEEE EDL 16-6 (1995) p. 230-232.
Ke Wang et al, Towards Circuit Integration on Fully Flexible Parylene Substrates, proceedings of the 31st Annual International Conference of the IEEE EMBS, Minneapolis, Minnesota, USA, Sep. 2-6, 2009, p. 5866-5869.
J.F. Creemer et al, MEMS hotplates with TiN as heater material, IEEE Sensors pp. 4, 2005.
K.R. Williams et al, Etch Rates for Micromachining Processing—Part II, Journal of Microelectromechanical Systems, vol. 12, No. 6, Dec. 2003.

* cited by examiner

TWO-TERMINAL CMUT DEVICE

This application is the U.S. National Phase application under 35 U.S.C. § 371 of International Application No. PCT/EP2015/077995, filed on Nov. 30, 2015, which claims the benefit of EP Application Serial No. 14197268.7, filed Dec. 11, 2014. These applications are hereby incorporated by reference herein.

FIELD OF THE INVENTION

This invention relates to a ultrasound system comprising: an ultrasound array including at least one capacitive micromachined ultrasonic transducer device comprising a membrane coupled to a first electrode, a substrate opposing the membrane with a gas or vacuum cavity there between and coupled to a second and a third electrodes, wherein the second electrode opposes the first electrode in a peripheral region and the third electrode opposes the first electrode in a central region; at least one drive circuit coupled to the array and adapted to (a) bring the membrane into a collapsed state in which the membrane is collapsed to the substrate in the central region, by applying a DC voltage over the first and the third electrodes of the at least one CMUT device, and (b) activate the CMUT device by applying an AC voltage having a CMUT operating frequency over the first and the second electrodes of the at least one said CMUT device. Further this invention relates to a CMUT device for use in the ultrasound system and a manufacturing method of the CMUT device according to the present invention.

BACKGROUND OF THE INVENTION

A commonly known capacitive micromachined ultrasonic transducer device is tens of micrometer size diaphragm-like cell comprising two electrodes opposing each other. For transmission the capacitive charge applied to the electrodes is modulated to vibrate/move the diaphragm (membrane) of the device and thereby transmit a sound wave. Objects placed in the way of the sound wave propagation reflect the wave. The reflected sound wave causes vibrations of the membrane, modulating the capacitance between two electrodes of the CMUT transducer, thereby generating an electric signal. This signal is representative for the reflected sound wave hitting the membrane.

One of the ways to drive a CMUT device is so called "collapsed mode" described in U.S. Pat. No. 8,203,912 B2. The DC actuation voltage applied across both electrodes is large enough deflect the membrane electrode towards the substrate electrode such that the membrane is brought into a physical contact with the substrate electrode and forms a collapsed area. An AC component applied between the electrodes is used to move the active area (not in contact) of the membrane. Schematically a CMUT device can be modeled as two capacitors in parallel. An active area capacitor $C_a$ formed by an active area, wherein $C_a$ value varies with the distance between the membrane electrode and the substrate electrode. A collapsed area capacitor $C_c$ is formed by the collapsed area, and is constant for a given DC voltage. The latter capacitance is relative large, because of the small distance between the electrodes in the collapsed area. A large ratio between $C_c$ and $C_a$ has negative effect on an ultrasound array operating efficiency, wherein the array comprises these CMUT devices. In transmit mode, $C_c$ forms an unwanted capacitive load to the driver, causing high currents to flow back and forth that do not contribute to acoustically emitted power. Practical implementations of transmitters may convert this power to heat, thus, resulting in overheating and efficiency loss. This may limit the possibilities to integrate transmitters onto the CMUT array. In receive mode, the acoustic power that is converted to electrical energy should go to the receiver. However, the large capacitor, $C_c$, in parallel to the variable capacitor acts as a low pass filter to this signal, reducing sensitivity of the device.

One of the ways to partially address these disadvantages is described in U.S. Pat. No. 8,203,912 B2. A three-terminal capacitive micromachined ultrasonic transducer device includes a substrate electrode split in two electrodes arranged in central and peripheral areas: a first electrode and a second electrode. The first and the second electrodes are arranged in laterally spaced relation within a common plane of the wafer. A membrane electrode located above the wafer includes a central region disposed in collapsibly spaced relation with the first electrode, and a peripheral region located outward of the central region and disposed in collapsibly spaced relation with the second electrode. The first electrode and the second electrode are suggested to be electrically separated from each other, such that different bias voltages can be applied between the first and the membrane electrodes; and the second and the membrane electrodes. Though this solution permits isolating the parasitic capacitance of the collapsed central area, where the membrane is collapsed towards the first electrode; a practical realization of the three-terminal CMUT brings an additional complexity into providing interconnects between the CMUT device and the CMUT associate drive electronics.

SUMMARY OF THE INVENTION

It is an object of present invention to provide an ultrasound system of the kind set forth in the opening paragraph which enables an improved and efficient voltage supply to the ultrasound array with a reduced technical effort.

According to the invention this object is realized by providing an ultrasound system, wherein in at least one capacitive micromachined ultrasonic transducer device the third electrode, is electrically coupled to the second electrode, via a high impedance resistor having an impedance value higher than an AC impedance between the first and the second electrodes, when the membrane is in the collapsed state and the CMUT devices is activated at operating frequency.

This advantageous design of the ultrasound system provides a reduced, down to two, amount of terminals required to drive the CMUT device. The high impedance resistor, which has an impedance value higher than an impedance value of the AC-impedance between the first and the second electrodes, redistributes the impedance loads for the AC and DC sources. This high impedance value of the resistor reduces the ac-current flow through the DC-impedance load such that in the first approximation the AC source drives impedance determined by the active area capacitor, Ca. This design simplifies electrical scheme requirements to the CMUT device and interconnects, since only one DC source per CMUT device (or a number of CMUT devices) is needed. Thus, only two-terminals may be used to drive the CMUT device.

In an embodiment of the present invention the second electrodes and the third electrodes of two or more capacitive micromachined ultrasonic transducer devices in the array are coupled to a single high impedance resistor.

This embodiment describes a case, wherein the high impedance resistor is shared between two or more CMUT devices. The second electrodes from multiple CMUT devices can be coupled to the corresponding third electrodes of these devices via the same high impedance resistor. This configuration may be beneficially used in a high focused ultrasound (HIFU) application, wherein multiple CMUT devices may be driven by one signal.

In another embodiment of the present invention the high impedance resistor has an impedance value in between 10 kOhm and 5 MOhm or in particular in between 500 kOhm and 1 MOhm.

This embodiment describes an application of the suggested ultrasound system in a wide range of the operating frequencies: from 1 MHz to 15 MHz, for example. The impedance value in between 500 kOhm and 1 MOhm can provide in improved performance of the ultrasound system in a general imaging mode in the frequency range from 3 to 5 MHz.

In yet another embodiment of the drive circuit (45') comprises a DC voltage source and an AC voltage source.

The drive circuit can be realized combining separate DC and Ac voltage sources.

Yet in another embodiment of the present invention the high impedance resistor (R) comprises a thin film layer having a thickness equal or less than 7 nm or in particular in between 2 nm and 4 nm.

This embodiment provides one of the ways of realizing the high impedance resistor. Thin film layers having the reduced thickness (down to 7 nm or in between 2 and 4 nm) may provide impedance values higher than an impedance value of the AC impedance between the first and the second electrodes, when the device is operated in the collapsed state, for the most common medical ultrasound applications. An advantage of this embodiment is that the resistor comprising a thin layer can be easier integrated into the CMUT cell manufacturing flow.

In another embodiment of the present invention the thin film layer is TiN.

Thin layers of Titanium Nitride material show an increased resistivity with the reduced below 10 nm thickness. The resistivity of TiN thin film can vary from about 0.5 kOhm/square at 5 nm layer thickness up to about 5 kOhm/square at 2 nm layer thickness.

It is an object of present invention to provide a method for manufacturing a capacitive micromachined ultrasonic transducer device comprising:

providing a substrate;

providing a patterned electrode layer that defines a third and second electrodes embedded in the substrate;

defining a gas or vacuum cavity;

providing a membrane opposing the substrate with the gap there between;

providing a patterned first electrode layer embedded in the membrane;

providing an insulating layer that isolates the first electrode from the second and the third electrodes;

providing a thin film layer of a high impedance resistor by applying an atomic layer deposition (ALD) technique;

electrically coupling the third electrode with the second electrode via the high impedance resistor.

The method describes a manufacturing flow of the CMUT devices integrated with the high impedance resistor realized via thin film layer patterning, wherein the thin film is deposited using the ALD technique. The ALD technique provides controlled deposition conditions for the thin layer materials, which results in the defined thin layer thickness throughout the ultrasound array. The method may be implemented in the industrial manufacturing flow providing a high yield of the operational CMUT devices having comparable electrical characteristics.

In a further embodiment of the present invention the method further comprises a step of adjusting of a thickness and a material selection of the insulating layer (130) in order to vary a collapsed area capacitor (Cc).

In order to provide an additional stability in the CMUT device operation in the array a value of the collapsed area capacitor (Cc) can be varied. The possible ways to increase the Cc, for example, can be: reducing the thickness of the insulating layer, thus bringing the first electrode closer to the third electrode, when the membrane is in the collapsed state; or/and selecting the insulating material with higher dielectric constant, thus increasing the electrical filed in between the first and other electrodes.

These and other aspects of the invention will be apparent from and elucidated with reference to the embodiments described hereinafter.

DETAILED DESCRIPTION OF EMBODIMENTS

Figure 1:
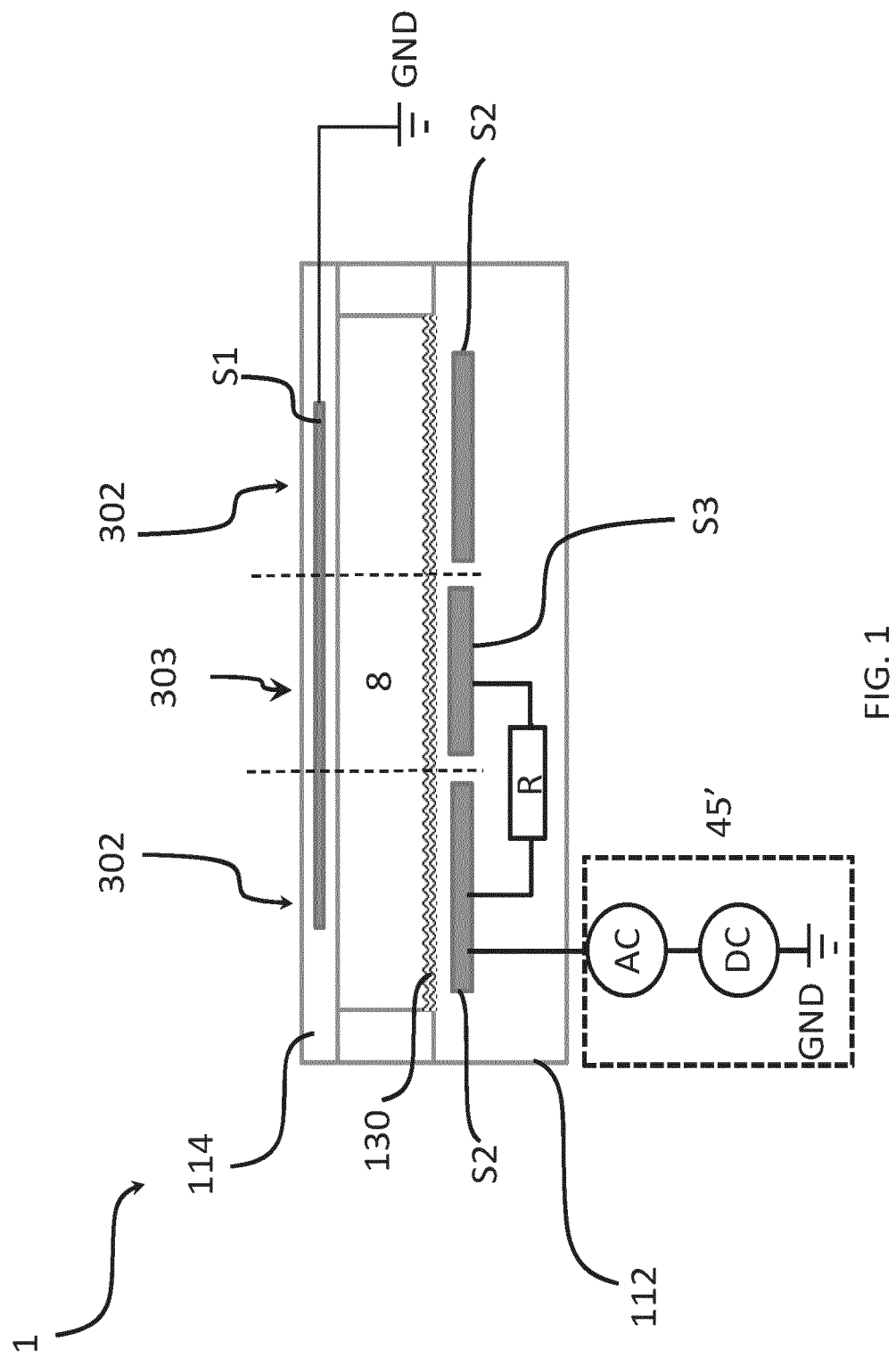
FIG. 1 illustrates a cross section of a CMUT device comprising two-terminals in accordance with the present invention.

In an implementation of the present invention the elements of an ultrasound transducer array 10' (FIG. 7) comprise CMUT device. FIG. 1 shows an embodiment of a CMUT device 1 according to the invention. A flexible membrane or diaphragm 114 is suspended above (opposing) a substrate 112 with a gap 8 there between. The substrate can be made of either silicon or another CMOS compatible material such as glass. A first electrode S1 is coupled to the cell membrane 114 and can move with the membrane 114. In the embodiment shown in FIG. 1 a second electrode S2 is embedded into the substrate 112 in a peripheral region 302 of the CMUT cell. A third electrode S3 of the CMUT device is embedded into the substrate 112 opposing the first electrode S1 in a central region 303. Other realizations of the electrode S1 design can be considered, such as electrode S1 may be embedded in the membrane 114 or it may be deposited on the membrane 114 as an additional layer. In this example, the membrane layer 114 is fixed relative to the top face of the substrate layer 112 and configured and dimensioned so as to define a spherical or cylindrical cavity 8 between the membrane layer 114 and the substrate layer 112. The second S2 and the third S3 electrodes may be arranged in laterally spaced relation within a common plane of the substrate 112. The second electrode S2 may be configured in a ring shape within the peripheral region 302 and the third electrode S3 me be circularly configured within the central region 303 forming a concentric circle with the ring shaped third electrode S3.

The cell and its cavity 8 may have alternative geometries. For example, cavity 8 could define a rectangular or square cross-section, a hexagonal cross-section, an elliptical cross-section, or an irregular cross-section. Herein, reference to the diameter of the CMUT cell shall be understood as the biggest lateral dimension of the cell.

Substrate electrodes: the second S2 and the third S3 electrodes are typically insulated on its cavity-facing surfaces with an additional insulating layer 130. A preferred insulating layer is a silicon dioxide (SiO2) dielectric layer deposited in a tetra ethyl oxysilane (TEOS) based PECVD process, formed above the third electrode B and below the first electrode S1. An alternative material for the insulating layer 130 can be oxide-nitride-oxide (ONO), high-k dielectrics and oxides (aluminium oxide, various grades including silane, SiH4, based PECVD SiO2). High-k dielectrics and oxides can be also deposited using atomic layer deposition (ALD) technique. The insulating layer may advantageously reduce charge accumulation which can lead to device instability and drift and reduction in acoustic output pressure. Use of the insulating layer is desirable with CMUTs with collapsed membrane, which will be described hereinafter with reference to FIG. 2. This type of CMUT is more susceptible to charge retention than CMUTs operated with suspended membranes. The disclosed components may be fabricated from CMOS compatible materials, e.g., Al, Ti, nitrides (e.g., silicon nitride), oxides (various grades: thermal or TEOS/SiH4 LPCVD/PECVD based), oly-silicon and the like. In a CMOS fabrication, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C. Exemplary techniques for producing the disclosed cavity 8 involve defining the cavity in an initial portion of the membrane layer 114 before adding a top face of the membrane layer 114. In the exemplary embodiment depicted in FIG. 1, the diameter of the cavity 8 may be larger than the diameter of the second electrode S2. The second S2 and the third S3 electrodes may be annular and coaxial spaced relative to a center of the CMUT cell. These electrodes may be formed during the same patterning step of a deposited conductive material.

The CMUT fabrication process can comprise either the "sacrificial release process", wherein the cavity underneath of the membrane is formed by first applying a sacrificial layer on the substrate, then applying the membrane layer followed by the removing of the sacrificial layer with a selective etchant; or the "wafer bonding process", wherein the cavity is formed on the prime wafer and the membrane in another wafer, then both wafers are bonded together such as the cavity confined by the membrane is formed (B. T. Khuri-Yakub, J. Micromech. Microeng. 21 (2011) 054004).

In accordance with principles of the present invention the CMUT device 1 comprises a high impedance resistor R, which electrically couples the second S2 and the third S3 electrodes. The CMUT device 1 further comprises an AC-source and a DC-source coupled to the second electrode S2.

The first electrode S1 and opposing it the second S2 and third S3 electrodes, which are electrically coupled to each other via the resistor R, of the CMUT cell provide the capacitive plates of the CMUT device and a gap of the cavity 8 in combination with the additional insulating layer 130 form the dielectric between the plates of the capacitor.

The spacing between the opposite electrodes (S1 and S2/S3) is controlled by applying a DC bias voltage to the second electrode S2 from the DC-source. For transmission the first electrode S1 and the second electrode S2 are driven (controlled) by a drive circuit 45' whose a.c. signal (voltage) causes the membrane to vibrate and transmit an acoustic signal. The drive circuit 45' can include separate DC and AC voltage sources as shown in FIG. 1. The substrate 112 of the CMUT cell 1 can be coupled to a top surface (not shown) of the application specific circuitry (ASIC) layer. Though in FIG. 1 the drive circuit 45' is depicted as a separated element, it shall be understood that the drive circuit 45' may be implemented as a part of the circuitry electronics provided by ASIC. The CMUT cell can be either manufactured on top of the ASIC in a sequence of CMOS processes or attached to the ASIC through a flip-chip technique, for example.

Figure 2:
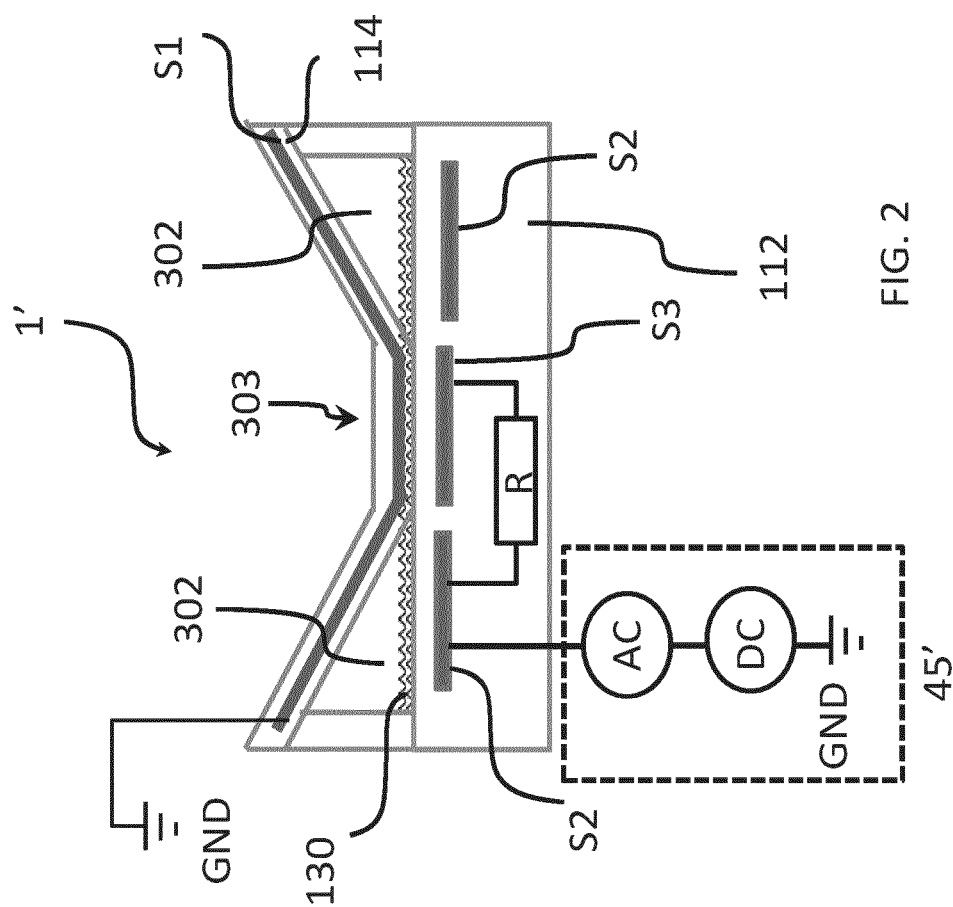
FIG. 2 illustrates a CMUT device operating in the collapsed mode, wherein a cell membrane is collapsed to a substrate, FIG. 3 (*a*) schematically depicts a simplified electrical model of the two-terminal CMUT device in accordance with the present invention; (*b*) schematically depicts a simplified electrical model for the embodiment, wherein the second electrodes and the third electrodes of two or more capacitive micromachined ultrasonic transducer devices in the array are coupled to a single high impedance resistor, FIG. 4 (*a*) illustrates a top view of a high impedance resistor having a meander shape; (*b*) illustrated a close view of the contact pad suggested for the meander shape high impedance resistor.

FIG. 2 illustrates a preferred example of the CMUT device 1' operation in the collapsed more, wherein the membrane 114 of the CMUT device 1' is collapsed towards the substrate in vicinity of the central region 303. During the collapsed mode of operation a part of the membrane 114 is in contact with the substrate around the central region 303 and its suspended portions (located in the vicinity of the peripheral region 302 and defined here as an active area) can be adapted to move/vibrate under applied electrical signal.

Figure 3:
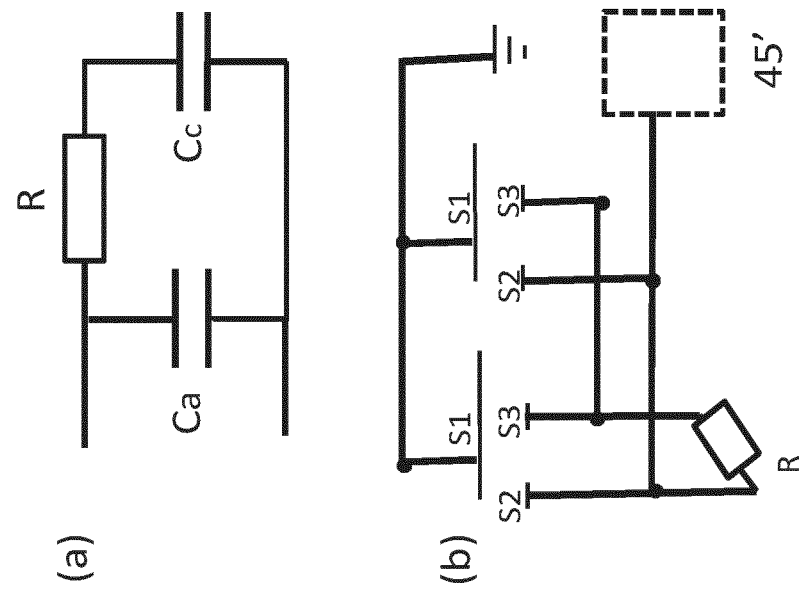

A simplified electrical model of the CMUT device 1' is schematically shown in FIG. 3(a). The CMUT device can be modeled as the active area capacitor $C_a$, formed by the active area, connected in parallel with the high impedance resistor R and the collapsed area capacitor $C_c$, formed by the collapsed area. In this model the input impedance of the CMUT device is $$Z = (ZaZrc)/(Za + Zrc) = Za \bigg/ \bigg( \frac{Za}{Zrc} + 1 \bigg),$$

wherein $Za=1/(2\pi fCa)$ is an impedance caused by the active area capacitor hereafter also called as an AC impedance between the first and the second electrodes; and $Zrc=R+Zc=R+1/(2\pi fCc)$ is a sum of the resistance value of the high impedance resistor and an impedance caused by the collapsed area capacitor (Zc); and f is an operating frequency of the CMUT device.

In the conditions of the collapsed mode, when the membrane 114 is collapsed to the substrate 112, and the high impedance resistor having an impedance value higher than the AC impedance $R \gg 1/(2\pi fCa)$ the AC source component of the drive circuit 45' mainly drives a load determined by the AC impedance. In other words an ac-current component mainly flows through the AC-impedance between the first and the second electrodes. In this condition the DC-source charges the collapsed area capacitor through the high impedance resistor R.

In this arrangement, it may even beneficial to increase the value of Cc. As the DC-source is now connected to Cc via the high impedance resistor, it is the charge in Cc that can keep the membrane in collapsed state during the echo receive event, when the acoustic wave that hits the CMUT will tend to pull the cell membrane off the collapsed state away from the central region 303.

In a concrete example, the CMUT cell has a circular cross section with a diameter of 120 micrometers, membrane thickness of 3 micrometer, gap width (distance from the substrate to the membrane) of 300 nanometer, the insulating layer 130 thickness of 420 nanometer; and a dielectric constant of 4.3. For the DC-bias voltage below 80V, the collapsed area capacitance, Cc, of the CMUT device is roughly 0.17 pF. When the DC voltage value approaches 80V, the cell membrane touches the opposite side of the cavity and gets into the collapsed state. The collapsed area capacitance value changes stepwise to 0.3 pF. The Cc value increases with the increase of the DC voltage value due to the increase in the collapsed region area. The active area capacitance, Ca, is about 10 times lower than the Cc value. Taking the value of Cc as 0.4 pF (at about 140V DC-voltage); the value of Ca as 0.04 pF (ten times lower than Cc); the operating frequency of the CMUT device is 5 MHz, the lower limit of impedance for the high impedance resistor is $1/(2\pi fCa) \approx 8$ MOhm. For the given CMUT cell design, the impedance of the high impedance resistor shall be above 8 MOhms in accordance with the principles of the present invention.

Using the same parameters for the calculation we estimate the impedance values of the resistor for different frequencies:

| f (MHz) | R (MOhm) |
|---------|----------|
| 1       | 4        |
| 3       | 1.32     |
| 10      | 0.4      |
| 15      | 0.25     |

One needs to keep in mind that the active area capacitance may vary with the medical application, for example 0.05 to 0.5 pF per device. Thus, at 5 MHz the AC impedance would be between 60 and 600 kOhm. In the preferred embodiment, the high impedance resistor value (R) may be several times higher than Za, for example 500 kOhm to 1 MOhm. The lower limit of R may be chosen based on the acceptable dissipation for a given CMUT array operation.

In another embodiment the high impedance resistor is shared between two or more CMUT devices arranged in the ultrasound array. A simplified electrical model of this embodiment is shown in FIG. 3(b). The second electrodes from two CMUT devices can be coupled to the corresponding third electrodes of these devices via the same high impedance resistor (R). This configuration permits reducing the lower limit of the high impedance resistor used for the "sharing" CMUT devices compared to the AC-impedance value of a single CMUT device, since now a total AC impedance is determined by the AC impedances of each sharing device connected in parallel.

This embodiment may be beneficially used in a high focused ultrasound (HIFU) application or ultrasound ablation therapy, wherein multiple CMUT devices in the array may be driven by one signal supplied by the driven circuit 45'.

Figure 5:
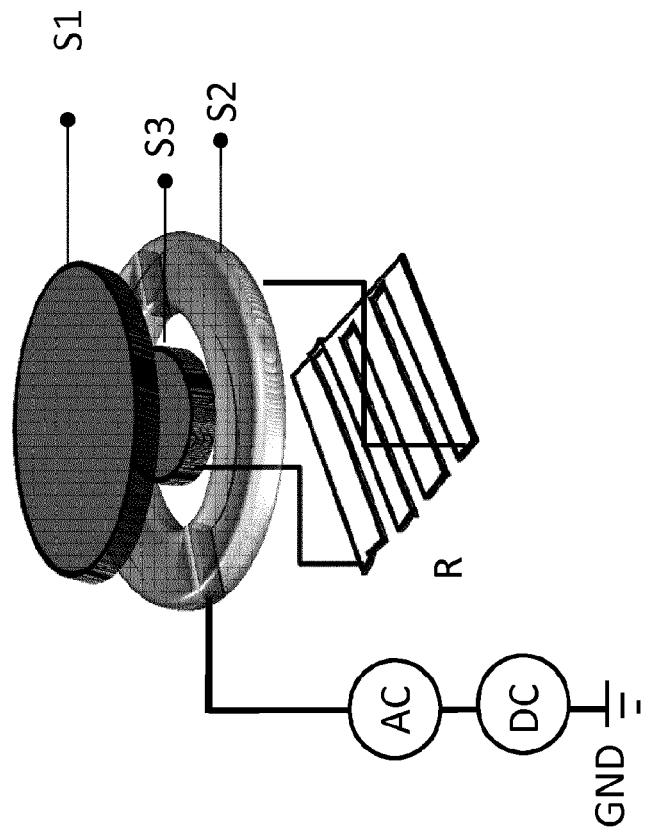
FIG. 5 illustrates a respective representation of the CMUT device comprising an integrated high impedance resistor.

Further we describe a way of integrating the high impedance resistor R into the CMUT device. FIG. 4(a) illustrates a top view of the high impedance resistor having a meander shape. The meander shape provides a compact arrangement for the resistor that can be disposed on the substrates (112) in the vicinity of the CMUT cell, such that the third and the second electrodes of the CMUT device can be electrically coupled to the resistor via the contact pads illustrated in FIG. 4(b). A three dimensional representation of the circular cross section CMUT device comprising concentric electrodes (S1, S2, S3) with the integrated high impedance resistor R is illustrated in FIG. 5.

In the monolithic integration approach, ultrasound sensor arrays are manufactured on top of the CMOS chip. This may significantly limit the number of available processing steps; the main limitation may come from maximum allowable processing temperature which needs to be kept below 450 C.

In the next embodiment we describe a method of manufacturing an integrated high impedance resistor R using a thin film layer technology. The resistance of thin films can be described in terms of 'sheet resistance' (Rsh) in Ohm/sq, where the resistance of a line with width w and length l is defined Rsh*l/w. The factor l/w is abbreviated as the number of (unit) squares. Rsh is related to the resistivity (ρ in [Ohm·cm]) and film layer thickness (t in [cm]) as Rsh=ρ/t.

The main challenge for the thin film application in the high impedance resistor implementation is controlled film quality and stability required throughout the manufacturing steps. In order to make thin films with Rsh>200 Ohm/sq, ultra thin films (<10 nm) are required. Manufacturing of these thin films in a reproducible way is difficult with Plasma Vapor Deposition (generally used for the deposition of 'thin' films of a few 10s up to 100s of nm's); for ultra thin film the thickness may difficult to control as the equipment is operated at the threshold of their sensitivity (power/gas flows etc). Moreover, many metals may oxidize when exposed to air (or even residual oxygen/$H_2O$ in vacuum systems). Metals that are considered 'oxidation resistant' (in bulk) owe that property to a thin native oxide (typically a few nm's) that stops diffusion of oxygen to the surface to prevent further oxidation. For many applications, this oxide is neglected. For sub-10 nm thin films however, the native oxide is a significant part of the layer. Hence the resulting thin film resistance depends on it (A. W. Groenland, *Nanolink-based thermal devices: integration of ALD TiN thin films*, PhD thesis, University of Twente, 2011, ISBN 978-90-365-3213-6; H. Van Bui et al, *Ultra-Thin Atomic Layer Deposited TiN Films: Non-Linear I-V Behaviour and the Importance of Surface Passivation, Journal of Nanoscience and Nanotechnology*, Vol. 11, 8120-8125, 2011).

Thus, a careful selection of a thin film material and its deposition method to be integrated into the CMUT manufacturing flow needs to be addressed.

Titanium Nitride (TiN) can be used as one of the materials for the thin film realized high impedance resistor. The resistivity of ultrathin TiN film deposited by means of the atomic layer deposition (ALD) is described in H. Van Bui, *Conduction and electric field effect in ultra-thin TiN films*, Appl. Phys. Lett. 103, 051904 (2013). It is observed that the TiN resistivity is a function of the film thickness and increases exponentially with a reduced thickness of the film layer.

For example, a high impedance resistor may be manufactured using a 2.5 nm thick ALD TiN layer showing the sheet resistance of 1600 Ohm/sq and a temperature coefficient of resistance of about 0/K that is compatible with the CMOS post processing. For application in the CMUT device, peak currents of 120 μA (60V over 500 kΩ) may be expected, resulting in a maximum current density of about $5*10^6$ A/cm$^2$. Although for soft metals like aluminum or copper this is the onset of electromigration, the ALD TiN layers show higher stability at these density currents (W.

Groenland et al, *Four Point Probe Structures With Buried and Surface Electrodes for the Electrical Characterization of Ultrathin Conducting Films*, IEEE TRANSACTIONS ON SEMICONDUCTOR MANUFACTURING, VOL. 25, NO. 2, MAY 2012).

Figure 6:
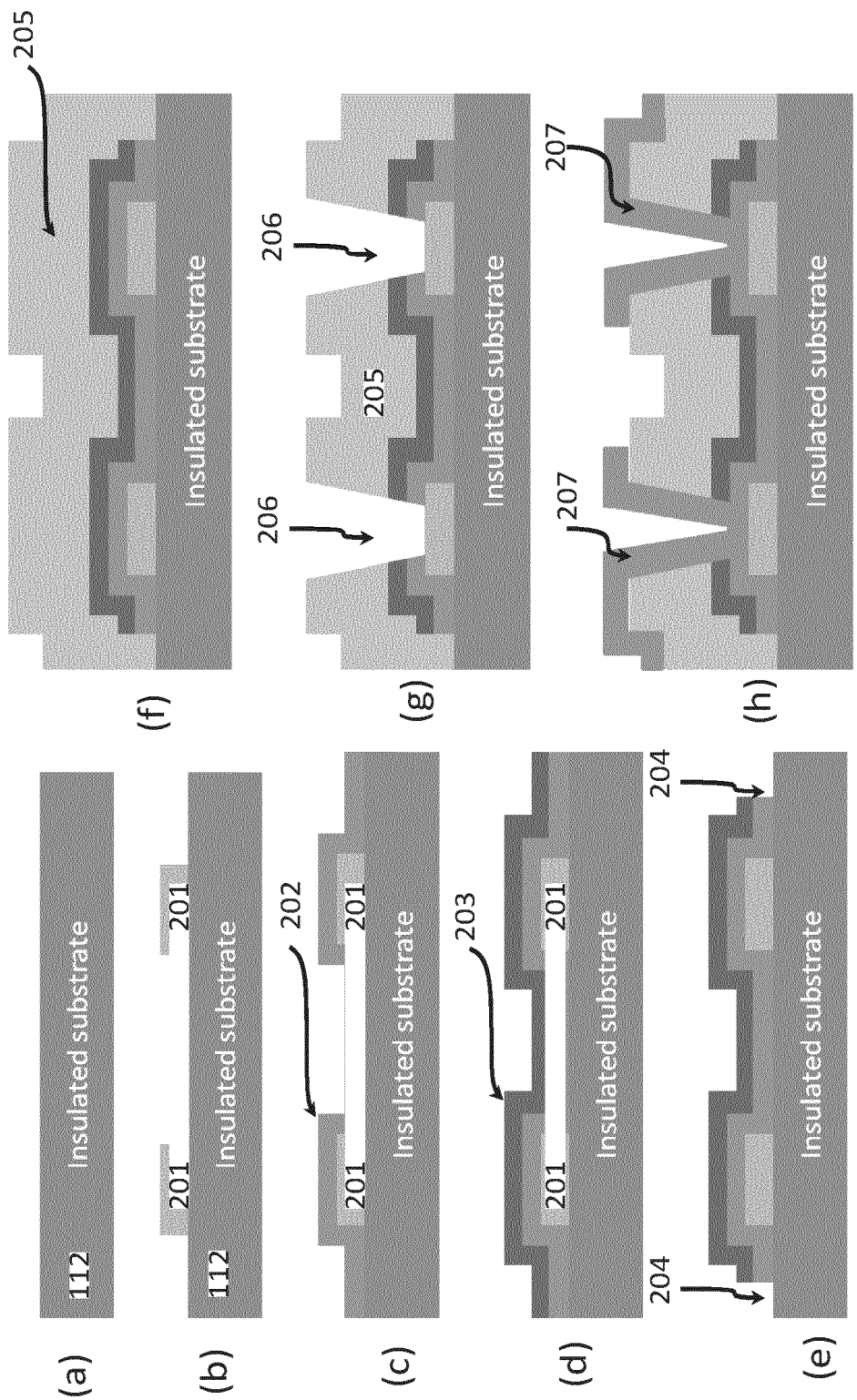
FIG. 6 depicts a manufacturing flow of the high impedance resistor.

In preferred embodiment the thin layer thickness of TiN can be less than 7 nm in particular from 2 to 4 nm. It shall be noted the given thickness corresponds to a non-oxidized thin film. In case of a partly oxidized thin film (which may happen on the grain boundaries, thereby rapidly increasing the resistance) a thicker TiN thin film can be used (10 nm or more). A manufacturing steps flow of the high impedance resistor is shown in detail in FIG. 6. In step (a) an insulating substrate 112 is provided. In case of a monolithic integration with an ASIC, the substrate 112 may already comprise buried integrated circuitry. Step (b) illustrates a deposition of the etch stop layer 201. A double layer of Ti/Pt with a thickness of 5/20 nm correspondingly may be chosen as the etch stop layer 201. It has a low topography, low oxidation, good $TiCl_4$ nucleation in ALD and can be patterned with lithography in combination with ion beam etching or a lift-off technique. Alternatively, TiN or TiW can be used, patterned with wet chemical or dry etching processes. Further, the thin film layer of TiN 202 is deposited by the ALD from $TiCl_4$ and $NH_3$ gases in step (c). The exact deposition conditions depend on pressure (typically $2-3*10^{-2}$ mBar) and pulse timing (typically 2 s of $TiCl_4$ and 2 s of $NH_3$ exposures). For a 2.5 nm ALD thin film of TiN a typical number of $TiCl_4/NH_3$ cycles is 300, however the deposition rate (Å/cycle) may be equipment specific, as well as the initial nucleation regime. To ensure the stability of the thin film layer a passivation layer 203 is deposited on top of the TiN layer without a vacuum break in step (d). Examples of the passivation layers are 15 nm of a-Si or $AL_2O_3$. Step (e) illustrates a patterning step using a photolithography for example. This step defines a shape of the high impedance resistor by releasing the substrate parts 204 from the previously deposited layers. step (f) comprises a deposition of a relatively thick inter-metal dielectric 205, for example 0.5-2 micrometer PECVD TEOS. The thickness of the layer may be chosen to minimize capacitive coupling with the CMUT electrodes (S2 and S3, for example) that is deposited on top of this layer. In step (g) vias 206 down to the etch stop layer 201 are created by using wet or dry etching for example. The electrical contact is provided by deposition and patterning of contact metal layer 207 in step (h). The contact metal layer can be aluminum (about 290 nm thick) that is wet chemically patterned with photoresist.

If the sacrificial release process is used for the CMUT fabrication the contact metal layer 207 may form a patterned electrode layer of the CMUT device, which will further define the second S2 and the third S3 electrodes embedded in the substrate 112. Further, standard steps of the CMUT fabrication may be used.

Figure 4:
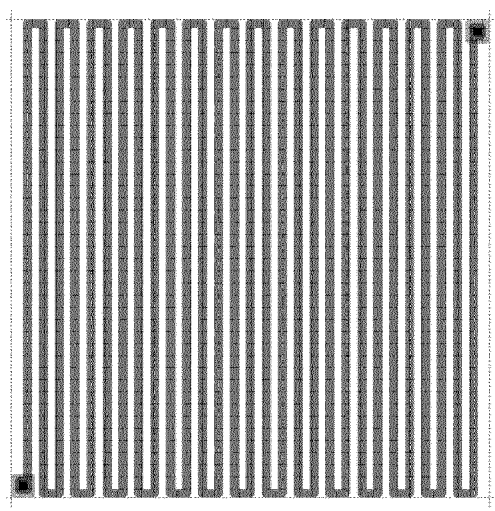
Figure 4:
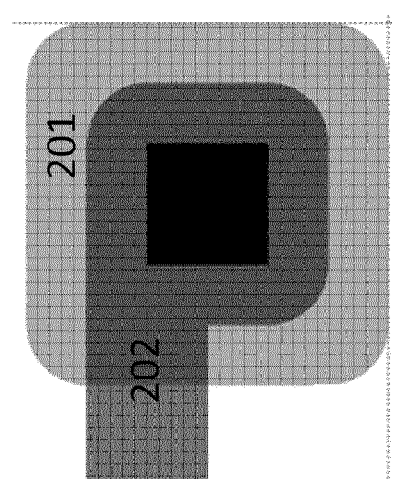

The meander shaped high impedance resistor in FIG. 4(*a*) has lateral dimensions of 60 by 60 micrometer and can be integrated with the CMUT device having a diameter of 60 micrometer as illustrated in FIG. 5. The close-up top vie of the contact pad shown in FIG. 4(*b*) with the etch stop layer 201 and contact via 206 (contact metal for connection is omitted). For the ALD TiN thin film layer of 2.5 nm thickness, the resistor of this dimensions has a length of 1700 sq and provides an impedance of about 2.7 MOhm.

It shall be understood by a person skilled in the art that the symmetrically interchanged configuration of the electrodes around the cavity 8 may provide a similar solution to the technical problem. Namely, the first electrode may be embedded in the substrate 112, while the second and third electrodes can be a part of the flexible cell membrane 114.

Figure 7:
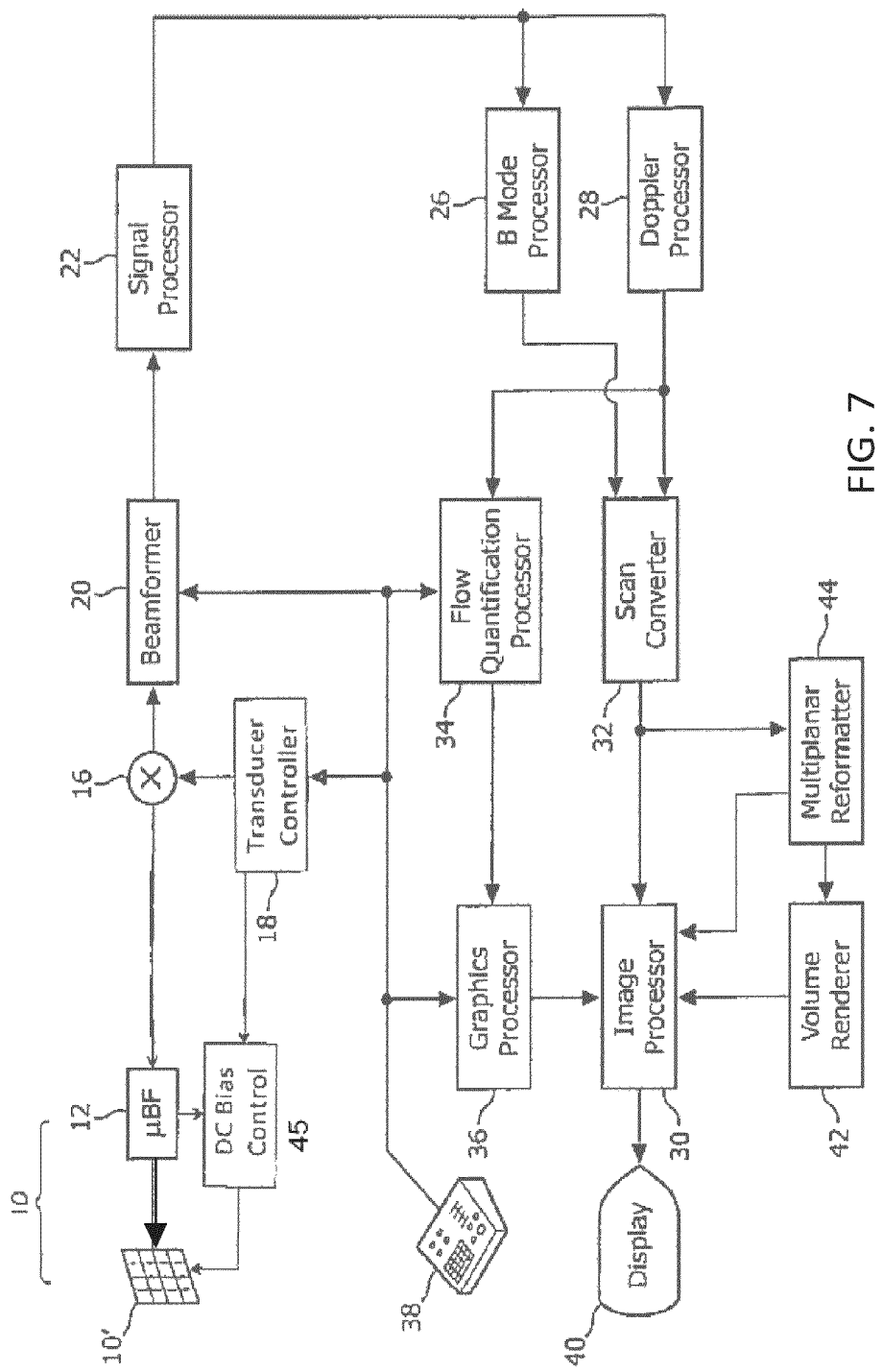
FIG. 7 illustrates in block diagram form an ultrasonic imaging system arranged to be operated in accordance with the principles of the present invention.

Referring to FIG. 7, an ultrasonic diagnostic imaging system with a CMUT array probe 10 is shown in block diagram form. The CMUT transducer array 10' is a two-dimensional array of transducer elements capable of scanning in a 2D plane or in three dimensions for 3D imaging. In case of 3D imaging and sometimes in 2D imaging the transducer array is coupled to a microbeamformer 12 in the probe which controls transmission and reception of signals by the CMUT array devices. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled to a transmit/receive (T/R) switch 16 which switches between transmission and reception modes. Transmission of ultrasonic beams from the transducer array 10 under control of the microbeamformer 12 is directed by a transducer controller 18 coupled to the T/R switch and the main system beamformer 20. Transducer controller 18 also receives input from the user's operation of the user interface or control panel 38. One of the functions controlled by the transducer controller is the direction in which beams are steered and focused. Beams may be steered straight ahead from (orthogonal to) the transducer array, or at different angles for a wider field of view. The transducer controller 18 can be coupled to control a DC drive circuit 45 for the CMUT array 10'. The DC drive circuit 45 controls a DC and AC source(s) for setting the voltage(s) that can be applied to the CMUT cells. The DC drive circuit may have the same functionality as the drive circuit 45' in FIG. 1 or can have an additional functionality depending on the medical application.

During reception the partially beamformed signals produced by the microbeamformer 12 (in case it is used) are coupled to a main beamformer 20 where partially beamformed signals from individual patches of transducer elements are combined into a fully beamformed signal. For example, the main beamformer 20 may have 128 channels, each of which receives a partially beamformed signal from a patch of dozens or hundreds of CMUT transducer cells. In this way the signals received by thousands of transducer elements of a CMUT transducer array can contribute efficiently to a single beamformed signal.

The beamformed signals are coupled to a signal processor 22. The signal processor 22 can process received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor may also perform additional signal enhancement such as speckle reduction, signal compounding, and noise elimination.

The processed signals are coupled to a B mode processor 26 and a Doppler processor 28. The B mode processor 26 employs detection of an amplitude of the received echo signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 28 receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow velocity values produced by the Doppler processor 28 and tissue structure information produced by the B mode processor 26 are coupled to a quantification processor 34. The flow quantification processor produces measure of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

The present invention is benefiting in terms of miniaturization. As every transducer CMUT cell requires only two-terminals (S1 and S3) for driving the CMUT device, moreover the high impedance resistor can be monolithically integrated into the CMUT device manufactured on top of the ASIC.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. An ultrasound system comprising:
an ultrasound array including at least one capacitive micromachined ultrasonic transducer device comprising a membrane coupled to a first electrode, a substrate opposing the membrane with a gas or vacuum cavity there between and coupled to a second and a third electrodes, wherein the second electrode opposes the first electrode in a peripheral region and the third electrode opposes the first electrode in a central region;
at least one drive circuit coupled to the array and adapted to (a) bring the membrane into a collapsed state in which the membrane is collapsed to the substrate in the central region, by applying a DC voltage over the first and the third electrodes of the at least one CMUT device, and (b) activate the CMUT device by applying an AC voltage having a CMUT operating frequency over the first and the second electrodes of the at least one said CMUT device; and
wherein
the third electrode of at least one capacitive micromachined ultrasonic transducer device of the array is electrically coupled to the second electrode via a high impedance resistor (R) having an impedance value higher than an AC impedance between the first and the second electrodes, when the membrane is in the collapsed state and the CMUT devices is activated at operating frequency.

2. The ultrasound system according to claim 1, wherein the second electrodes and the third electrodes of two or more capacitive micromachined ultrasonic transducer devices in the array are coupled to a single high impedance resistor.

3. The ultrasound system according to claim 1, wherein the high impedance resistor has an impedance value in between 10 kOhm and 5 MOhm or in particular in between 500 kOhm and 1 MOhm.

4. The ultrasound system according to claim 1, wherein the drive circuit comprises a DC voltage source and an AC voltage source.

5. The ultrasound system according to claim 1, wherein the high impedance resistor comprises a thin film layer having a thickness equal or less than 7 nm or in particular in between 2 nm and 4 nm.

6. The ultrasound system according to claim 5 wherein the thin film layer is TiN.

7. The ultrasound system according to claim 5, wherein the thin film layer is deposited by an atomic layer deposition (ALD) technique.

8. A capacitive micromachined ultrasonic transducer device comprising a membrane coupled to a first electrode, a substrate opposing the membrane with a gas or vacuum cavity there between and coupled to a second and a third electrodes, wherein the second electrode opposes the first electrode in a peripheral region and the third electrode opposes the first electrode in a central region;
- at least one drive circuit adapted to (a) bring the membrane into a collapsed state in which the membrane is collapsed to the substrate in the central region, by applying a DC voltage over the first and the third electrodes, and (b) activate the CMUT device by applying an AC voltage having a CMUT operating frequency over the first and the second electrodes; and
- wherein the third electrode is electrically coupled to the second electrode via a high impedance resistor having an impedance value higher than an AC impedance between the first and the second electrodes, when the membrane is in the collapsed state and the CMUT device is activated at operating frequency.

9. A method for manufacturing a capacitive micromachined ultrasonic transducer device comprising:
- providing a substrate;
- providing a patterned electrode layer that defines a third and second electrodes (S2) embedded in the substrate;
- defining a gas or vacuum cavity;
- providing a membrane opposing the substrate with the gap there between;
- providing a patterned first electrode layer that defines a first electrode embedded in the membrane such that the second electrode opposes the first electrode and the third electrode opposes the first electrode in a central region;
- providing an insulating layer that isolates the first electrode from the second and the third electrodes;
- providing a thin film layer of a high impedance resistor by applying an atomic layer deposition technique;
- electrically coupling the third electrode with the second electrode via the high impedance resistor.

10. The method for manufacturing the capacitive micromachined ultrasonic transducer device according to claim 9, wherein the step of defining the gas or vacuum cavity comprises one of: a sacrificial layer release process and a wafer bonding process.

11. The method for manufacturing the capacitive micromachined ultrasonic transducer device according to claim 10, wherein the high impedance layer comprises TiN layer.

12. The method for manufacturing the capacitive micromachined ultrasonic transducer device according to claim 10, wherein the step of providing the insulating layer comprises depositing a high-k dielectric layer with the ALD technique.

13. The method for manufacturing the capacitive micromachined ultrasonic transducer device according to claim 9, wherein all step of providing layers comprise the ALD technique.

14. The method for manufacturing the capacitive micromachined ultrasonic transducer device according to claim 9, further comprising a step of adjusting of a thickness and a material selection of the insulating layer in order to vary a collapsed area capacitor.

15. The method for manufacturing the capacitive micromachined ultrasonic transducer device according to claim 14, wherein the adjusting step causes an increase of the collapsed area capacitor via a reduction of the insulating layer thickness and a selection of a higher dielectric constant material.

* * * * *